(12) United States Patent
Layne et al.

(10) Patent No.: US 9,066,732 B2
(45) Date of Patent: Jun. 30, 2015

(54) METHOD AND APPARATUS FOR BONE REMOVAL

(75) Inventors: Richard W. Layne, Denver, CO (US);
Lawrence R. Jones, Conifer, CO (US);
David T. Stinson, Woodville, WA (US)

(73) Assignee: Crosstrees Medical, Inc., Boulder, CO (US)

( * ) Notice: Subject to any disclaimer, the term of this patent is extended or adjusted under 35 U.S.C. 154(b) by 1342 days.

(21) Appl. No.: 12/677,939

(22) PCT Filed: Sep. 15, 2008

(86) PCT No.: PCT/US2008/076464
§ 371 (c)(1),
(2), (4) Date: Dec. 30, 2010

(87) PCT Pub. No.: WO2009/036467
PCT Pub. Date: Mar. 19, 2009

(65) Prior Publication Data
US 2011/0093024 A1     Apr. 21, 2011

Related U.S. Application Data

(60) Provisional application No. 60/993,960, filed on Sep. 14, 2007.

(51) Int. Cl.
| *A61B 17/00* | (2006.01) |
| *A61B 17/16* | (2006.01) |
| *A61B 17/34* | (2006.01) |
| *A61B 19/00* | (2006.01) |

(52) U.S. Cl.
CPC ......... *A61B 17/1671* (2013.01); *A61B 17/1604* (2013.01); *A61B 17/16* (2013.01); *A61B 17/1659* (2013.01); *A61B 17/3472* (2013.01); *A61B 2017/0046* (2013.01); *A61B 2019/462* (2013.01)

(58) Field of Classification Search
USPC .................................................. 606/79–86 R
See application file for complete search history.

(56) References Cited

U.S. PATENT DOCUMENTS

| 5,015,255 | A | * | 5/1991 | Kuslich ......................... 128/898 |
| 5,062,845 | A | * | 11/1991 | Kuslich et al. .................. 606/80 |
| 5,697,889 | A | * | 12/1997 | Slotman et al. ............... 600/204 |
| 6,004,326 | A |   | 12/1999 | Castro et al. |
| 6,383,188 | B2 | * | 5/2002 | Kuslich et al. .................. 606/80 |
| 6,468,279 | B1 |   | 10/2002 | Reo |
| 6,485,496 | B1 |   | 11/2002 | Suyker et al. |
| 6,746,451 | B2 | * | 6/2004 | Middleton et al. .............. 606/79 |
| 7,063,705 | B2 | * | 6/2006 | Young et al. ................. 606/86 R |
| 7,429,264 | B2 | * | 9/2008 | Melkent et al. ............... 606/159 |
| 7,674,265 | B2 | * | 3/2010 | Smith et al. ..................... 606/79 |

OTHER PUBLICATIONS

International Search Report for PCT/US2008/076464, mailed Dec. 1, 2008.

* cited by examiner

*Primary Examiner* — Nicholas Woodall

(57) ABSTRACT

Methods and apparatus for surgical treatment of vertebrae, comprising a brush-like tamp component for addressing cancellous bone and a slider component that may be distally advanced over the brush-like tamp component while both are (preferably) aligned within a working cannula providing access to a drill channel within the vertebrae. Distal advancement of the slider creates a combination of it and the brush-like component. A handle provides mechanical advantage.

17 Claims, 13 Drawing Sheets

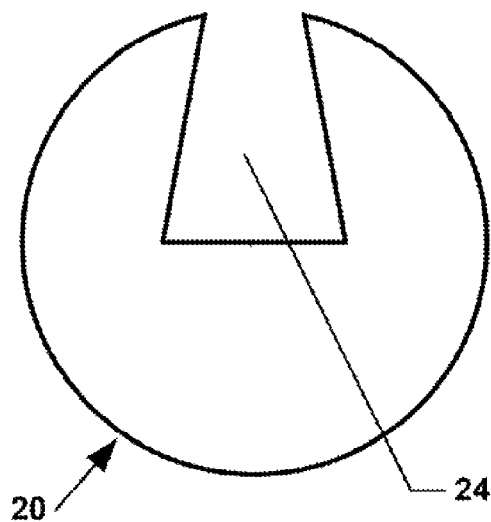
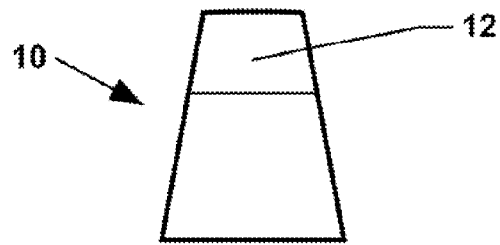
Figure 10A
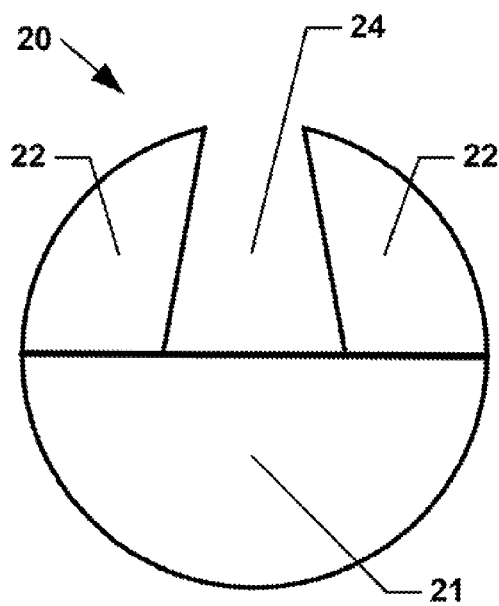
Figure 9A
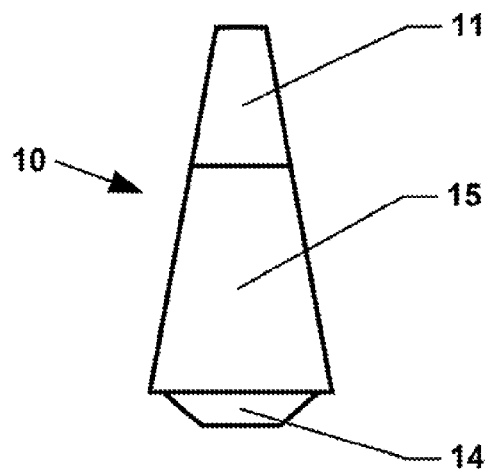
Figure 9B
Figure 10B

METHOD AND APPARATUS FOR BONE REMOVAL

This application claims priority to and the benefit under 35 U.S.C. §371 of PCT Application No. PCT/US2008/076464, filed Sep. 15, 2008, which claims priority to and the benefit of U.S. Provisional Application No. 60/993,960, filed Sep. 14, 2007, the disclosure of each of which is incorporated by reference herein in its entirety.

TECHNICAL FIELD

This application involves methods and apparatus for addressing cancellous bone within vertebrae.

BACKGROUND

Various orthopedic surgical procedures require access to the cancellous bone within vertebrae. Examples include vertebroplasty and kyphoplasty. Typically such procedures create such access by conventional steps of drilling an access hole through the vertebral wall, advancing the drill distally further into the cancellous bone itself, followed by withdrawal of the drill. The void so created in the cancellous bone is known as a drill channel for purposes of this application.

Subsequent surgical treatment of the vertebrae may require additional removal, compaction, tamping, or (in general) addressing in some manner the remaining cancellous bone within the vertebrae that surrounds the drill channel. A working cannula is typically inserted into the drilled hole in the vertebral wall to access the remainder of the drill channel with various tools and components that may be distally advanced into the vertebrae through the lumen of the cannula, and proximally withdrawn from the lumen when desired. The fixed inner diameter of the lumen places significant restraints on the dimensions of such tools and components.

SUMMARY

This application describes and claims methods and apparatus for surgical treatment of vertebrae, in which a brush-like tamp component addresses cancellous bone and a slider component is distally advanced over the brush-like tamp component while both are within a working cannula. The cannula provides access to a pre-existing drill channel within the vertebrae. Distal advancement of the slider creates a unified combination of it and the brush-like tamp component. In some embodiments, an optional handle may then be attached, while in other embodiments the handle is already affixed to the brush-like tamp component. In either case, the distal advancement of the slider causes the tamp to extend the size of the drill chamber in the transverse (radial) direction. Rotation and/or translation of the handle causes the tamp to further extend the size of the drill chamber within the cancellous bone.

BRIEF DESCRIPTION OF THE DRAWINGS

The accompanying drawings show a particular embodiment of the invention as an example, and are not intended to limit the scope of the claims.

FIG. 9A is an end view of the proximal end of the slider; FIG. 9B is an end view of the distal end of the slider.

FIG. 10A is an end view of the proximal end of the brush-like tamp component of the previously illustrated embodiment; FIG. 10B is an end view of the distal end of the same.

DETAILED DESCRIPTION

The following discussion accompanies the drawings, which schematically illustrate a particular embodiment solely for purposes of illustration. Thus, any reading of this discussion as limiting the scope of the claims is contrary to the intent of the inventors, who intend this discussion to describe and enable the full scope of all matters within the realm of the accompanying claims.

This application describes an apparatus that comprises a brush-like tamp component for addressing cancellous bone within the vertebrae, and a complimentary slider component for positioning that component in place. The slider may be distally advanced over the length of the tamp component until the two are aligned lengthwise. The mutual configuration of the two components provides the tamp component with access to the interior extent of the drill channel within the vertebrae. The distal advancement of the slider also creates a combination of it and the tamp component, to which an optional handle may be attached. Motion of the attached handle is thus transferred to the brush/slider combination, so that the two components move as a single unit corresponding to the motion of the handle, whether rotational around the common lengthwise axis of the combination, or for removing the combination by proximally directed removal from the cannula.

The overall function of these components, and thus the methods by which they are used, is illustrated in FIGS. 1-8, which sequentially illustrate use of certain embodiments of the components described above.

Figure 1:
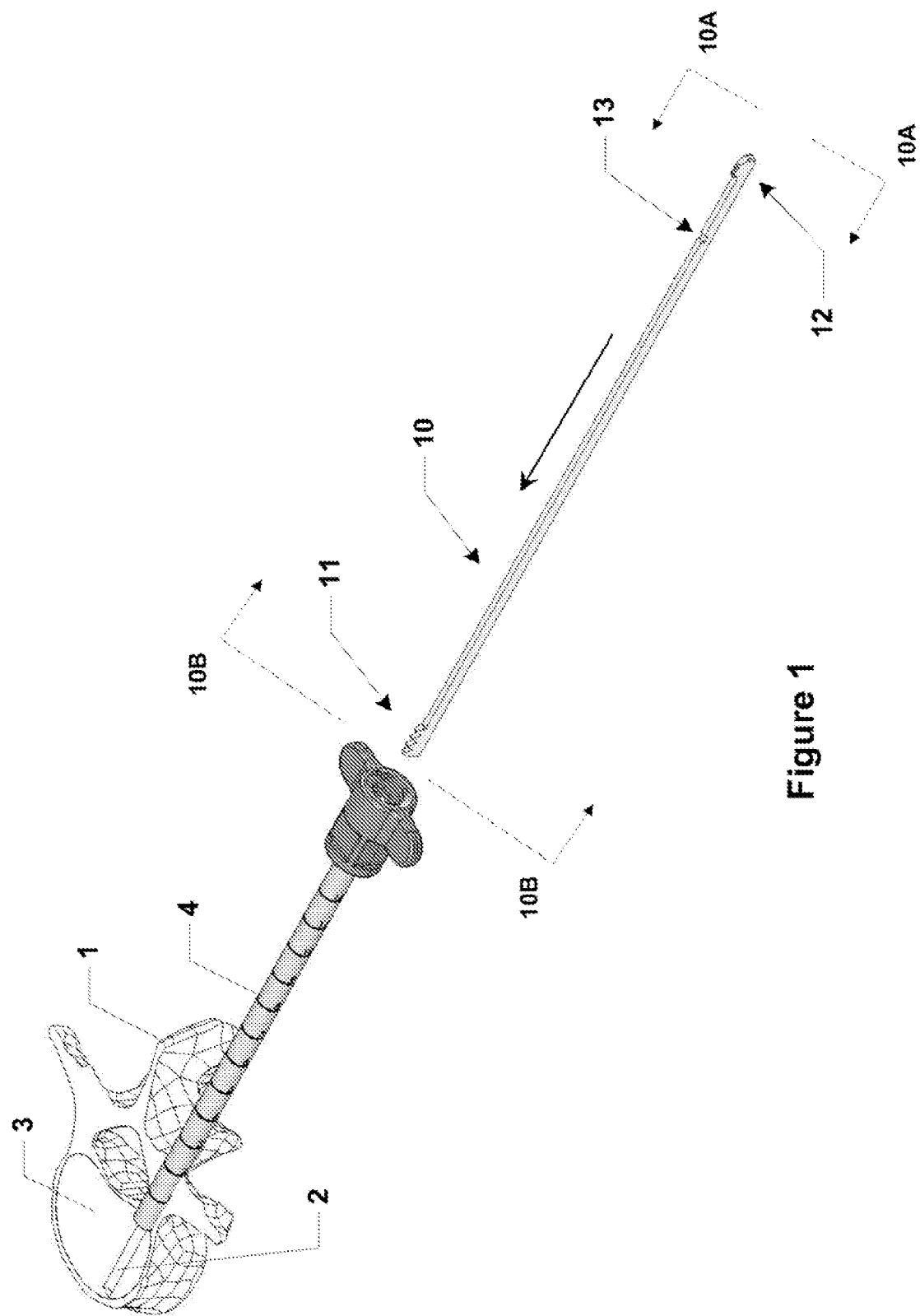
FIG. 1 is a schematic perspective view of a working cannula and an embodiment of a portion of an apparatus for addressing cancellous bone in intervertebral procedures.

Turning first to FIG. 1, the inferior portion of vertebrae 1 is shown in cross-section after drill channel 2 has been created within cancellous bone 3 and working cannula 4 has been deployed. Brush-like tamp 10 is illustrated before its distal lengthwise advancement (as illustrated by the arrow) into the central lumen of cannula 4.

Figure 2:
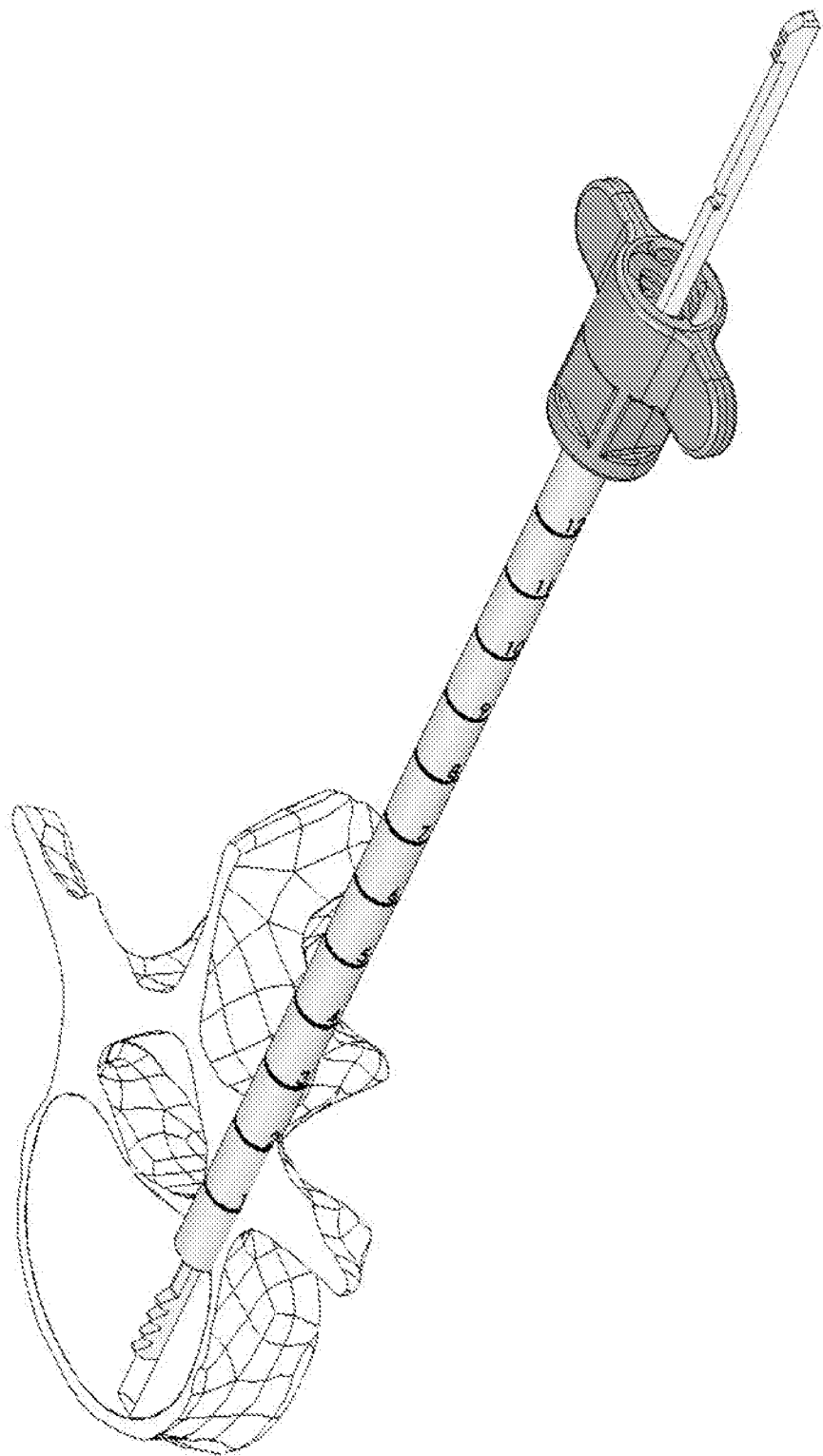
FIG. 2 is a schematic perspective view of the embodiment of FIG. 1, after the brush-like tamp portion of the apparatus has been distally advanced within the working cannula portion into a drill channel within the cancellous bone.
Figure 2A:
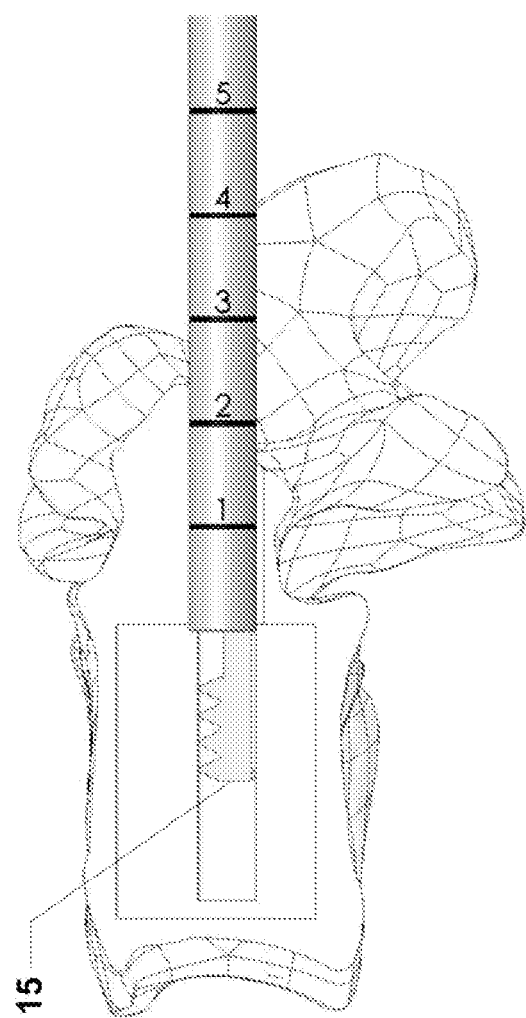
FIG. 2A is a side cross section of a portion of FIG. 2.

The result of such advancement is illustrated in FIGS. 2 and 2A. As suggested by FIG. 2A, the height of the textured surface formed by the features 11 of the distal portion of tamp 10 (described in greater detail below) is preferably no more than what is required to enable tamp 10 to reside within the cross-sectional height of drill channel 2 when tamp 10 lies on the lower (inferior) extent of drill channel 2. This preference enables tamp 10 to be easily inserted within drill channel 2 without engaging cancellous bone 3. The height could be reduced, but this would not be as effective a device.

Figure 3:
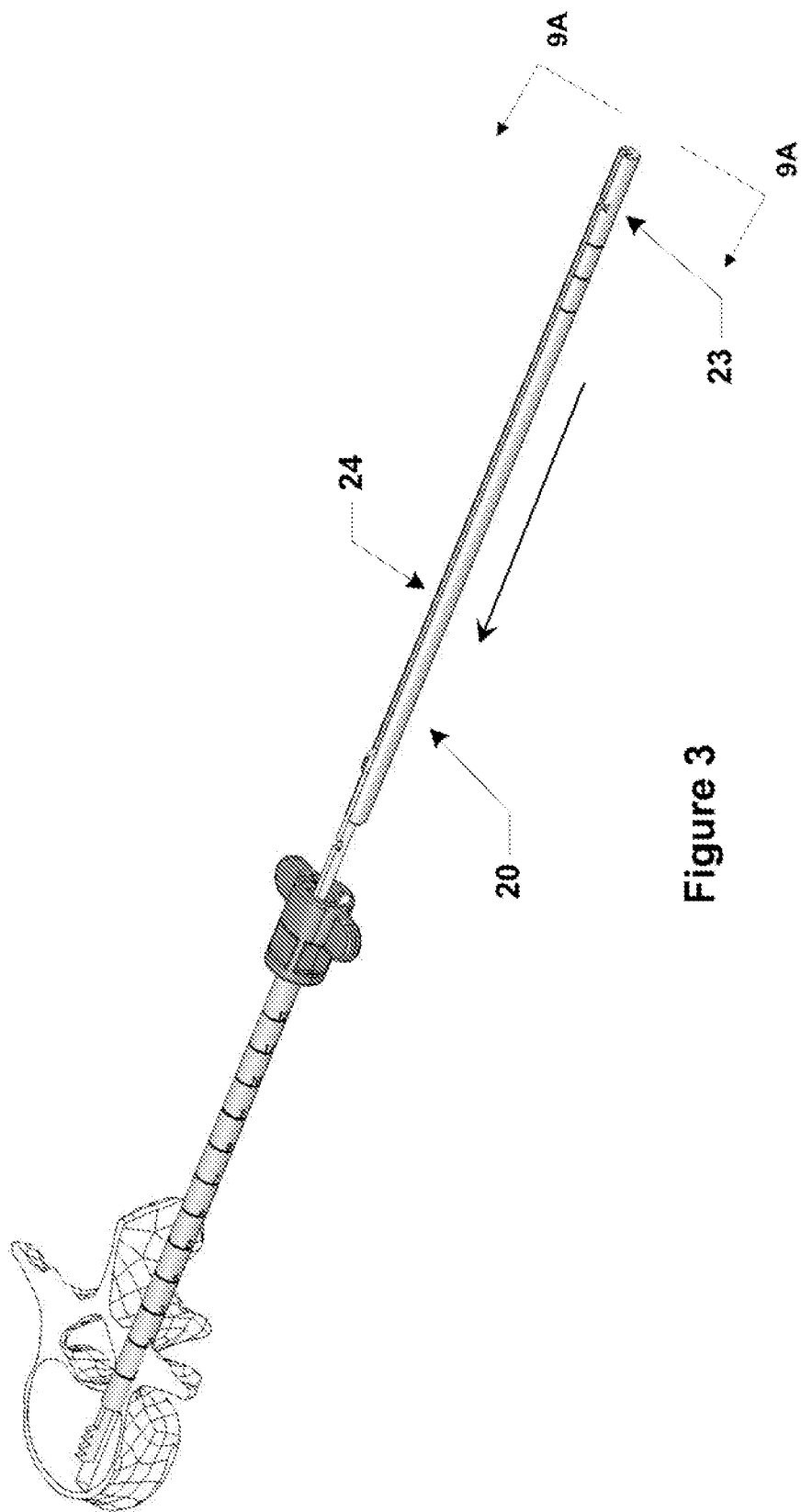
FIG. 3 is a schematic perspective view of the embodiment of the previous Figures, after the slider portion of the apparatus has been distally advanced over the proximal end of the brush-like tamp portion and then farther distally within the working cannula.

Tamp 10 extends proximally outward from cannula 4 even after it is distally advanced through working cannula 4 and into drill channel 1. Turning to FIG. 3, this enables slider 20 to be advanced distally over tamp 10 and thus distally lengthwise into cannula 4, again as indicated by the arrow. As explained in greater detail below, as slider 20 is so advanced, it forces the distal tip of tamp 10 (which bears textured features 11) outward beyond the inner extent of the superior (upper) portion of drill channel 2.

Figure 4:
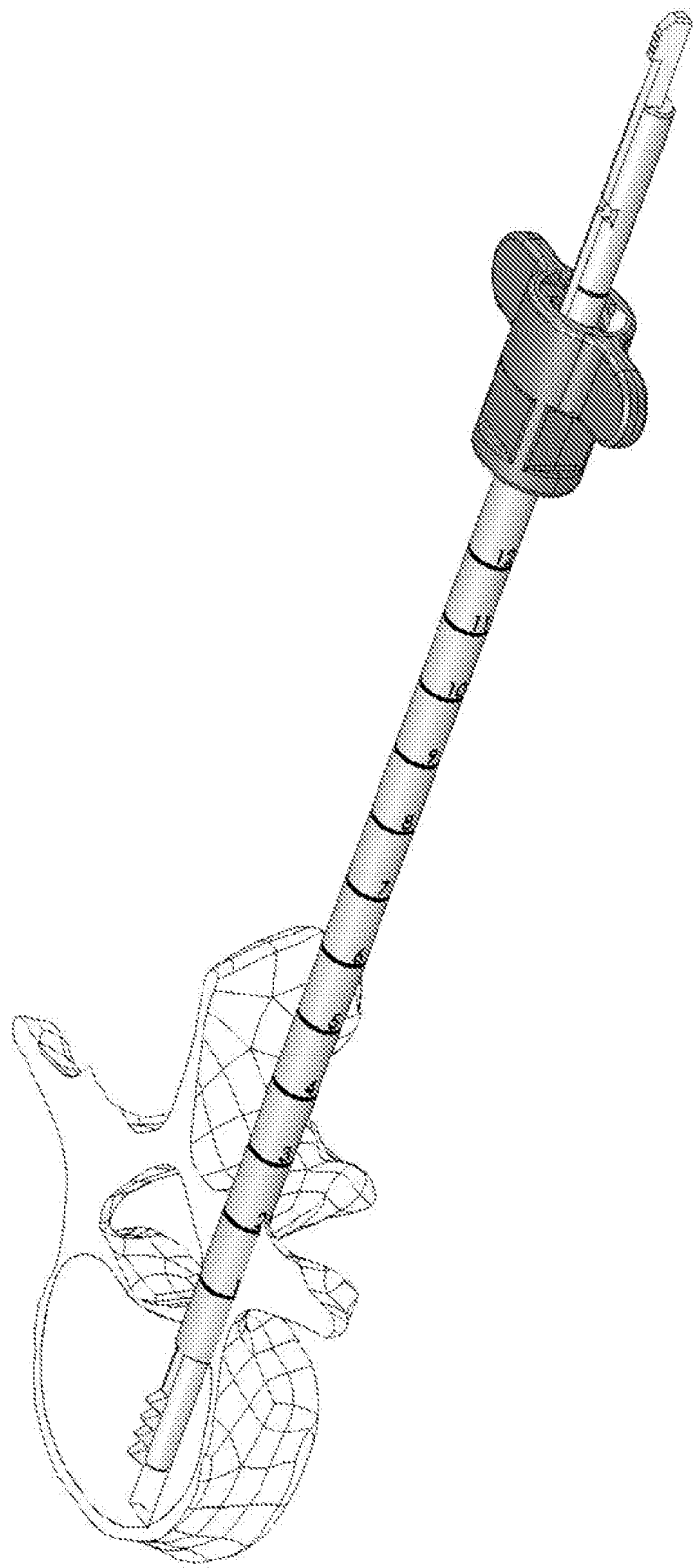
FIG. 4 is a schematic perspective view of the embodiment of the previous Figures, after the slider portion has been fully distally advanced and coupled to the distal end of the brush-like tamp portion.

The combination of the tamp 10 and slider 20 upon full advancement of the latter onto the former is shown in FIG. 4. Each component is notched (in the embodiment illustrated) or otherwise bears a feature or indicia to enable optional handle 30 to be added, as discussed below.

Figure 5:
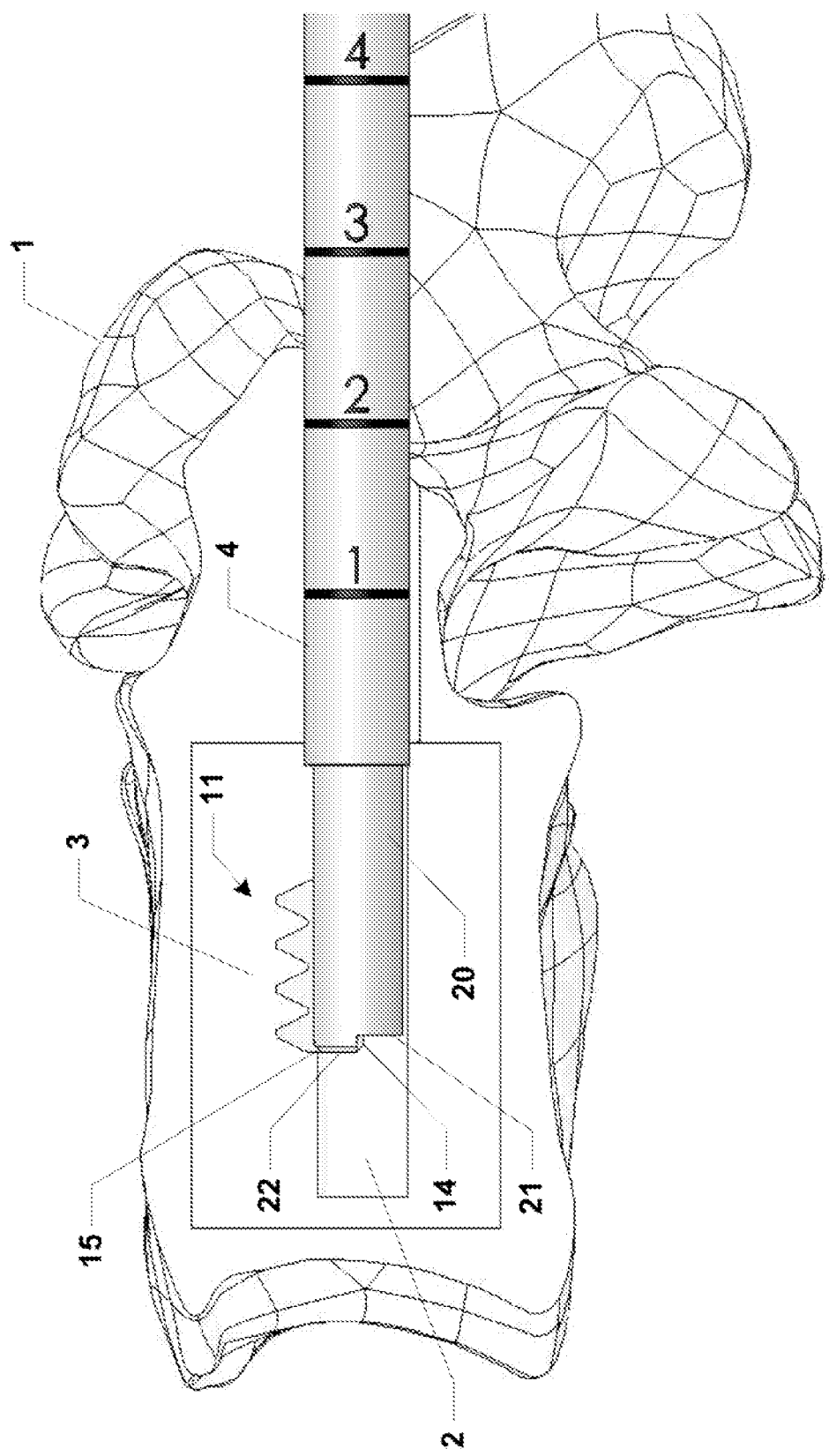
FIG. 5 is a side cross section of a portion of FIG. 4.

FIG. 5 illustrates that the full advancement of slider 20 onto tamp 10 is achieved when a distal end stop 14 of tamp 10 aligns with the lower distal end face 21 of slider 20. (See also FIGS. 9A and 10A.) This prevents slider 20 from advancing any further distally into drill channel 1 along the lengthwise (proximal-distal) axis.

As described below, the shape of slider 20 causes tamp 10 to move away from the lengthwise axis, into the cancellous bone that lies beyond the previous extent of the drill channel 1. As illustrated, this movement is in the superior direction, but the exact direction of movement depends on the angular orientation of tamp 10 within the lumen of working cannula 4.

Figure 6A:
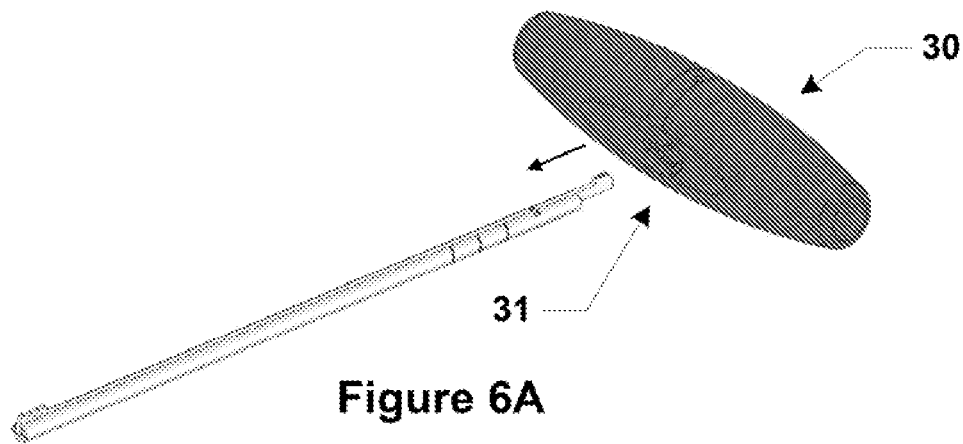
FIGS. 6A-6C are a sequence of schematic perspective views of the embodiment of the previous Figures, illustrating how an optional handle portion may be assembled to the coupled tamp/slider combination of FIGS. 4 and 5.
Figure 6B:
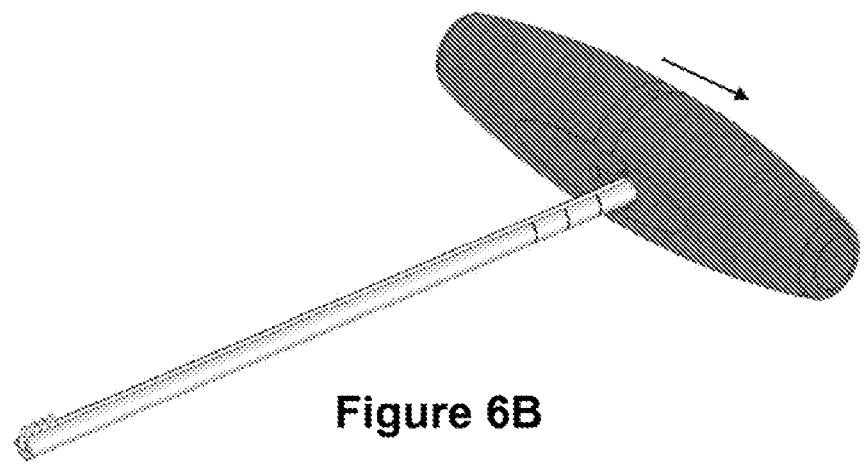
Figure 6C:
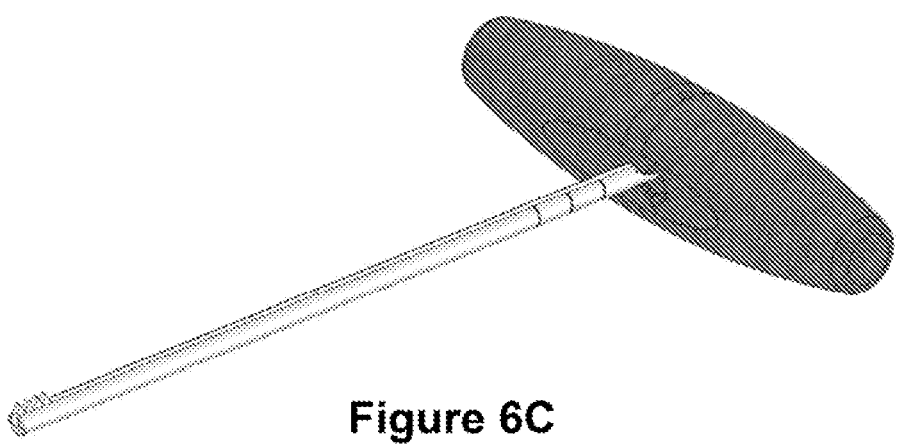

FIG. 6 illustrates the general procedure for attaching an optional handle 30 to the embodiment described above. Such a handle is an optional, but highly preferred, means for increasing the mechanical advantage that may be applied to the combination for rotation and/or translation of the combination. If sufficient mechanical advantage may be applied directly to the combination, a handle is not required. In the illustrated embodiment, handle 30 is attached to the combination by distally advancing it such that a complimentary keyhole 31 defined within the handle 30 surrounds a dovetail feature 12 formed in of the proximal end of the tamp 10, which proximal end proximally extends beyond the proximal end of slider 20. Then handle 30 is translated slightly to one side such that narrower portion of keyhole 31 locks onto the proximal end of the combination of tamp 10 and slider 20, engaging the proximal end of slider 20. One or more optional set screws (not illustrated) within handle 30, or their functional equivalent, may be used to hold handle 30 in this position, in accordance with known principles.

Figure 7:
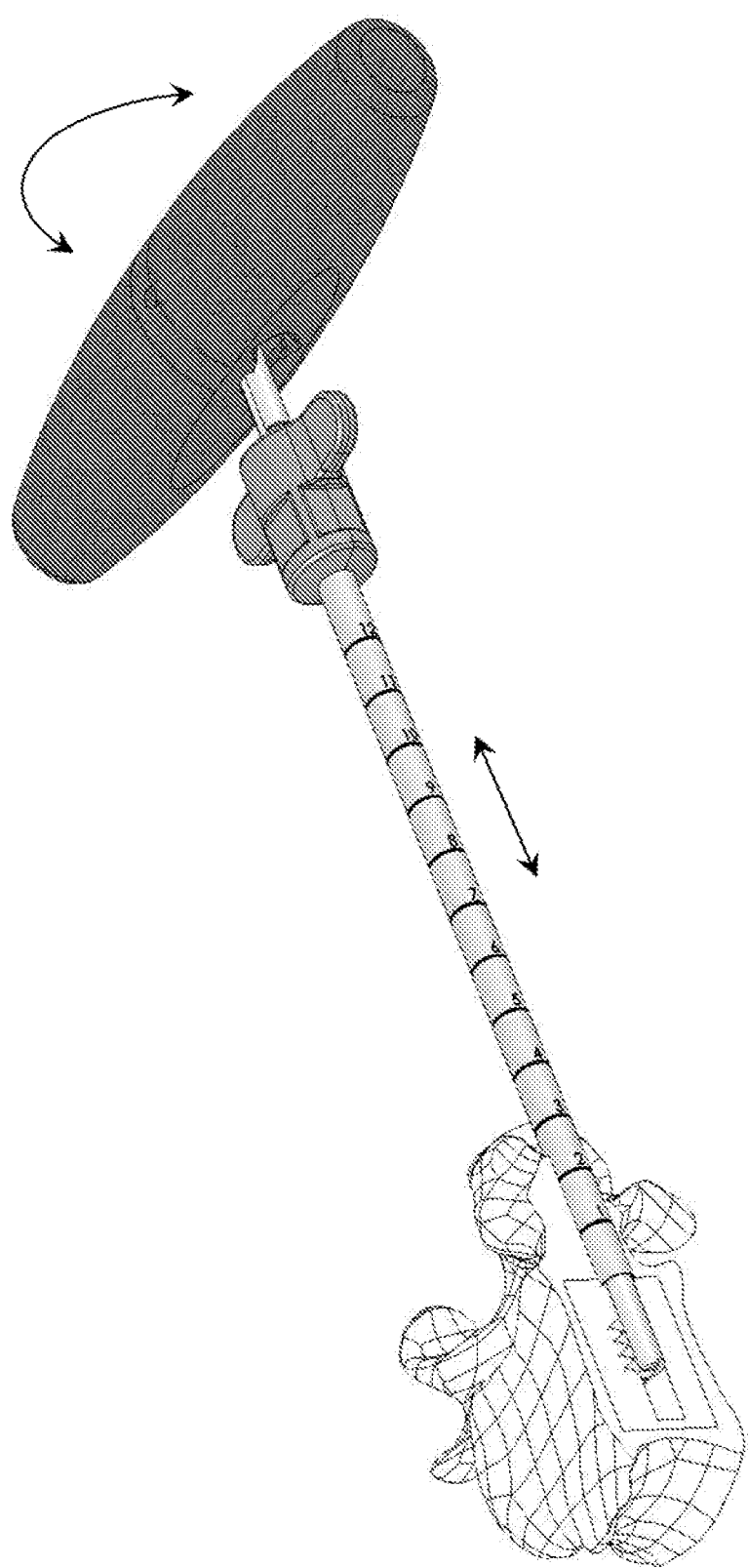
FIG. 7 is a schematic perspective illustration of the assembled apparatus of the previous Figures, illustrating use of the assembly within the vertebral body.
Figure 8:
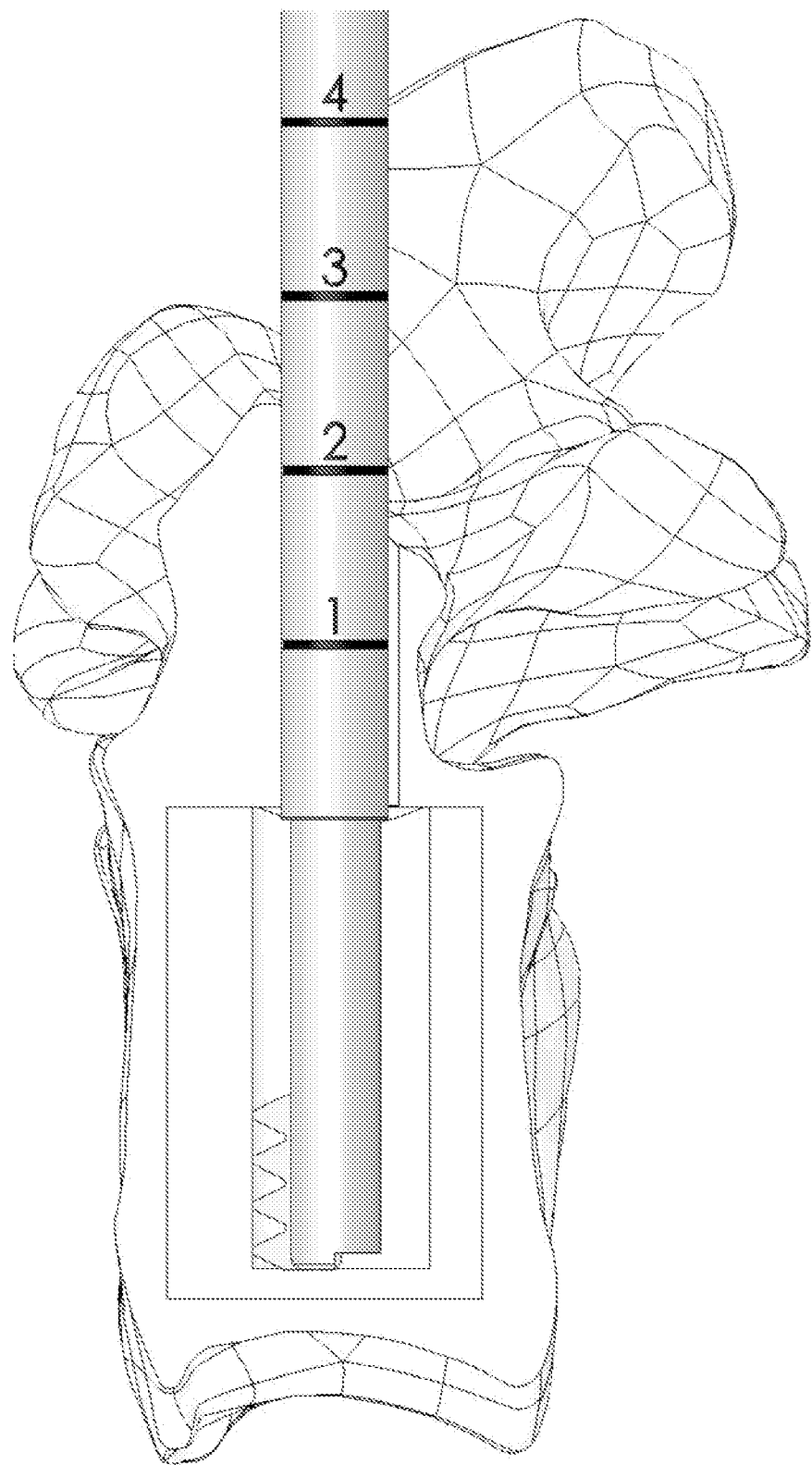
FIG. 8 is a schematic side cross-sectional view illustrating the result of use of the apparatus as depicted in the previous Figures.

FIG. 7 illustrates that rotation of the assembly (especially using the optional handle described above) enables the extent of the drill channel 1 to be expanded in the radial direction (i.e., away from the longitudinal axis of the assembly). FIG. 7 also illustrates that longitudinal motion of the assembly (especially using the optional handle described above) enables the extent of the drill channel 1 to be expanded in the proximal or distal directions (i.e., along the longitudinal axis of the assembly). These actions may be combined in any order or to any extent as the clinician sees fit. The result of such actions is shown in greater detail in FIG. 8.

In the embodiment described above, the details of the construction of each component may be described as follows. Tamp 10 is generally rectilinear in cross-section, and has three features of particular note. At the distal end of tamp 10, a serrated or otherwise textured surface is formed by a set of extensions 11, each of which addresses the extent of cancellous bone, as described above. In the embodiment illustrated, the set of extensions 11 is a series (four, as illustrated) of outwardly directed features, which may be a set of notches, bumps, or anything else that creates a complex surface capable of addressing the extent of cancellous bone such that the drill channel 1 is expanded.

At the proximal end of tamp 10, dovetail 12 is used to facilitate coupling of the optional handle 30. As illustrated, it comprises a generally rectangular, wider portion of the tamp 10 that includes a proximally directed face that is beveled (such as the 45° beveled face illustrated in the Figures) to guide optional handle 30 into proper combination with the apparatus.

A third feature of tamp 10 is notch (or equivalent) 13 near its proximal end, to facilitate alignment of tamp 10 with slider 20. Slider 20 bears a complimentary channel 24, as described further below.

The dimensions of tamp 10 and its various features are dictated to large extent by the clinical environment, and are not critical to the scope of the claims except as otherwise indicated. In the embodiment illustrated, tamp 10 is on the order of 22 cm in total length. The main shaft portion has generally uniform cross-section throughout its extent of 2.5 mm in cross-sectional height (neglecting the extensions 11 above) and 2.0 mm in cross-sectional width. The sides of tamp 10 are preferably angled inwardly such that tamp 10 is slightly wider at the bottom than at the top. The similarly shaped channel 24 in slider 20 thus prevents tamp 10 from slipping out of channel 24 once channel 24 is slid distally down the length of tamp 10.

Notch 13 is on the order of 1.0 mm in depth and 2.0 mm in length along the longitudinal axis of tamp 10. The proximal end of notch 13 lies on the order of 2.8 cm from the proximal end of tamp 10, although this dimension enters into the dimensions of the optional handle 30 and vice versa.

Each feature 11 is shaped generally like an equilateral triangle extending approximately 2.0 mm above the cross-sectional height of the shaft of tamp 10, for a total height of approximately 4.5 mm. Each feature 11 may bear a flattened surface to a on the order of 0.5 mm (measured along the length of tamp 10). The collection of the four features 11 is on the order of 1.0 cm in length extending proximally away from the most distal edge of the collection (i.e., the distal end of tamp 10).

A small end stop 14 (see also FIG. 5) at the distal end of tamp 10 extends away from tamp 10 in the inferior direction (as illustrated), i.e., the direction opposite that toward which the features 11 "point" with their generally triangular (but flattened) shapes. End stop 14 engages with the lower distal end face 21 of slider 20 to prevent slider 20 from advancing any further distally into drill channel 1.

Slider 20 is on the order of 20.5 cm in total length. The main shaft portion has generally uniform circular cross-section throughout its extent, and is 0.5 mm in diameter. Notch 23 of slider 20 is dimensioned and located to compliment notch 13 of tamp 10 and more particularly to align the two components together when slider 20 is advanced distally until end stop 14 engages the distal end face 21 of slider 20 as described above. Thus, notch 23 is also on the order of 1.0 mm in depth and 2.0 mm in length along the longitudinal axis of slider 20. The proximal end of notch 23 lies on the order of 1.5 cm from the proximal end of slider 20.

The lower distal end surface 21 of slider 20, which end stop 14 contacts, is recessed back from the upper distal end surface 22 of slider 20 by 1.0 mm (see also FIG. 5), i.e., the longitudinal dimension of end stop 14. This enables the upper distal end surface 21 of slider 20 to be flush with the distal end 15 of tamp 10.

Running down the entire length of slider 20 is a channel 24 having cross-sectional shape and dimensions to accommodate the corresponding features of tamp 10. As viewed from the end of slider 20, channel 24 extends only partially downward (in the inferior direction) from the uppermost (superior) surface of slider 20. The depth of channel 24 matches the height of the main shaft of tamp 10, i.e., 3.0 mm. This enables tamp 10 to fit neatly within the entire depth of channel 24, but not extend above the superior surface of slider 20, when slider 20 is positioned entirely down the length of working cannula 4. The result is a tightly assembled combination that behaves like a unitary member when rotated and/or translated to address the extent of the cancellous bone beyond drill chamber 1 as described above.

The length of tamp 10 that extends proximally from the proximal end of slider 20 is used to engage optional handle 30. In addition to the notches 13 and 23 that align with each other as described above, it is possible to incorporate an additional feature (such as an identically sized secondary notch 25) at another location of slider 20. This can aid in alignment of handle 30 onto slider 20. In the case of the keyhole arrangement within handle 30 described above, the location of the secondary notch 25 is directly opposite that of the combined notch 13 and 23, as this enables both sides of keyhole 31 in handle 30 to engage slider 20, thus providing a stronger fit between the two.

Optional handle 30 may be any convenient shape or material. A typical size is 12.5 cm in length, with a diameter of 7.5 mm at each end, gently increasing to 30.0 mm in the center.

Figure 11:
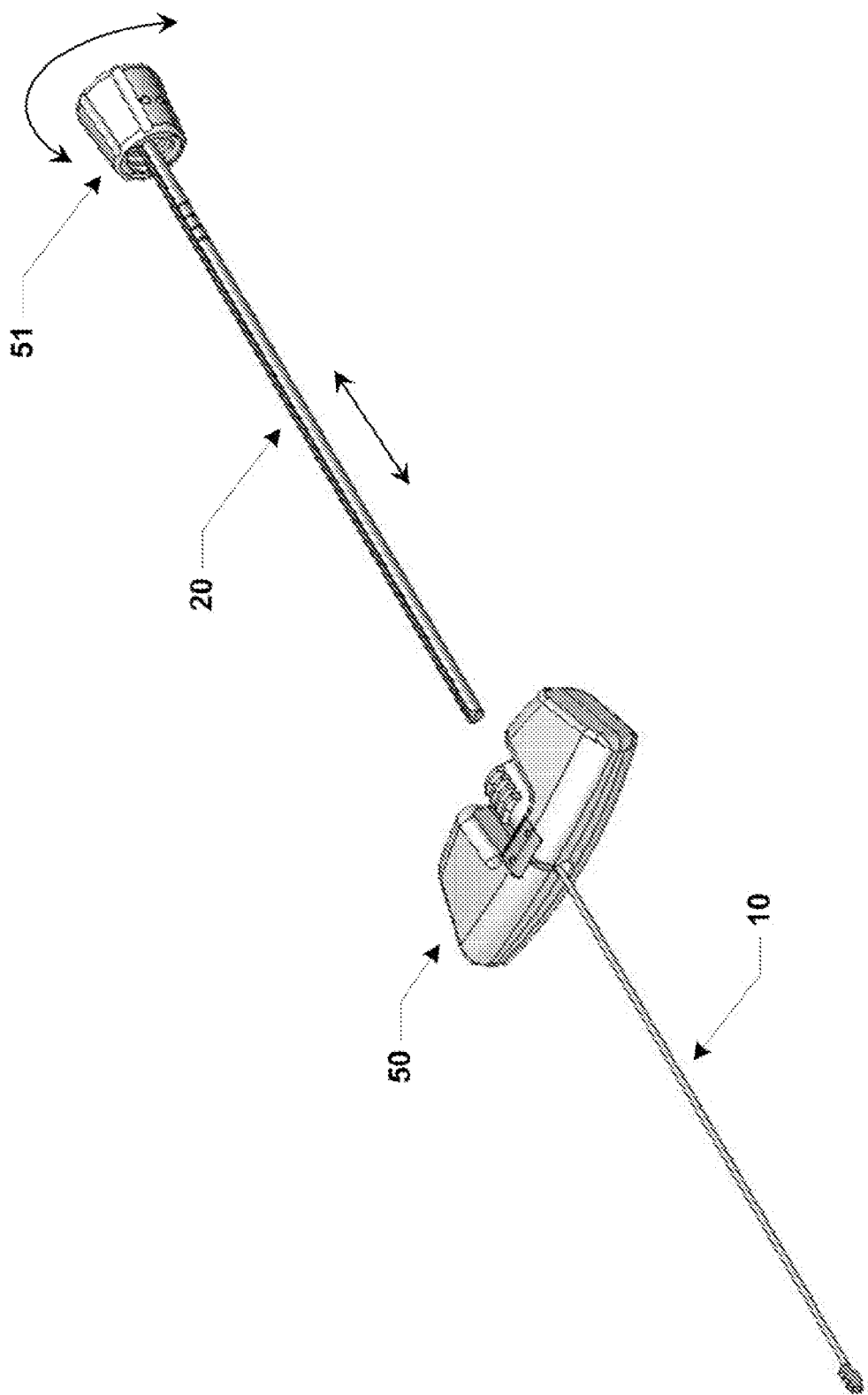
FIG. 11 is a perspective view of another embodiment.
Figure 12:
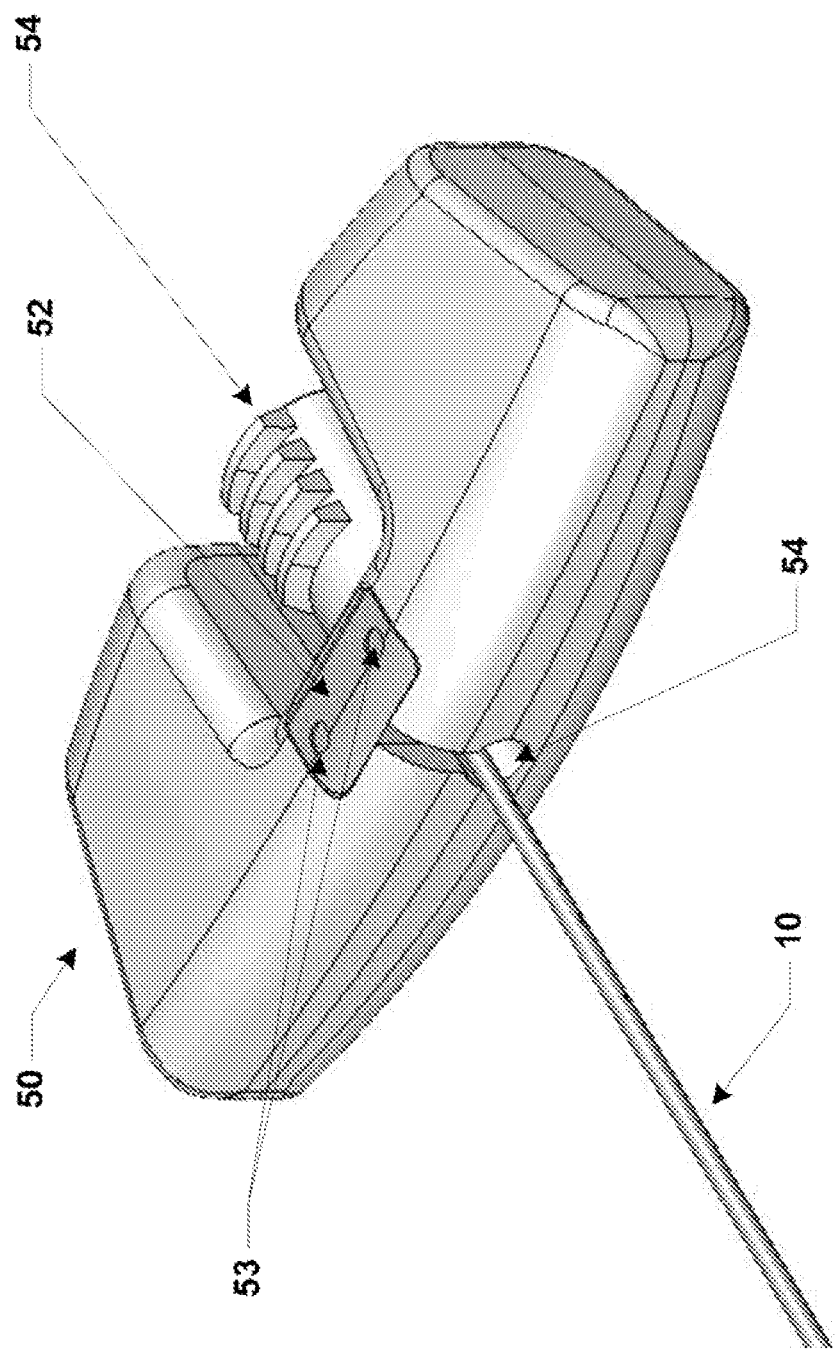
FIG. 12 is a perspective view of a portion of FIG. 11.
Figure 13:
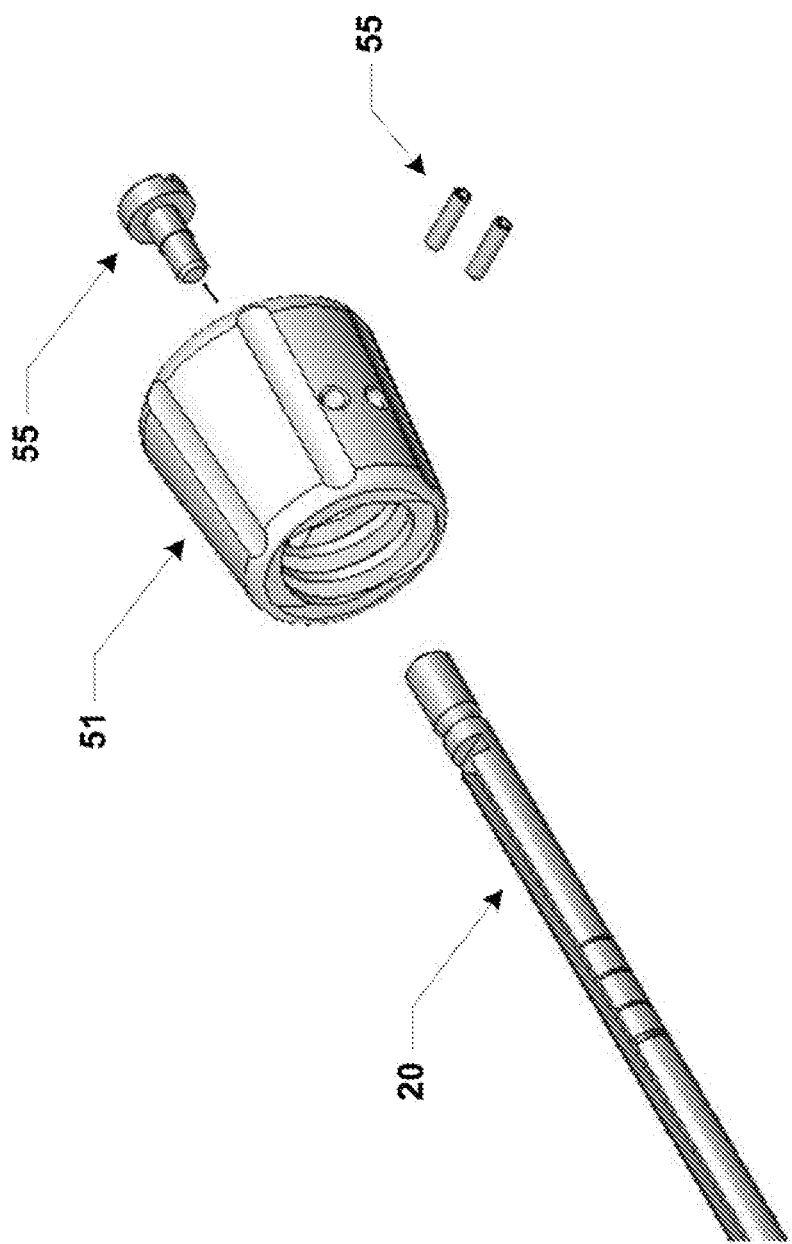
FIG. 13 is a perspective view of another portion of FIG. 11.

Another embodiment is illustrated in FIGS. 11-13, with the understanding that operating principles and the like that are common to the embodiment described above will not necessarily be repeated but will be understood to apply as appropriate.

As before, brush-like tamp 10 is advanced distally through a cannula (not shown) to the desired location; however, in this embodiment, handle 50 lies on the proximal end of tamp 10 as opposed to being added separately as described above, and thus handle 50 is used to advance tamp 10. Then, slider 20 is distally advanced through the central opening in handle 50, to engage tamp 10 as described before. Slider 20 comprises freely rotating top cap 51 at the distal end of slider 20. Top cap 51 is internally threaded (or otherwise designed) to engage complementary threads (or other features) on the proximal end of handle 50. Thus, when top cap 51 is threaded or otherwise attached to handle 50, slider 20 advances its final extent, lifting tamp 10 as described above and enabling handle 50 to rotate the entire unified assembly.

Handle 50 may be attached to the proximal end of tamp 10 by use of an appropriate mounting plate 52 and screws 53 to ensure proper alignment of tamp 10 within central opening 54, i.e., closely fitting to the uppermost portion of central opening 54 to ensure that slider 20 may pass beneath it as the latter is distally advanced. Mounting plate 52 could be separate from tamp 10 or integrated with it; use of a separate mounting plate enables each of tamp 10 and handle 50 to be available in various sizes, shapes and other configurations and then interchanged with each other, if desired.

Similarly, top cap 51 may be attached to freely rotate at the distal end of slider 20 by use of mounting screws 55 or any other equivalent mechanism that provides the proper tolerances, freedom of movement, and so on.

The materials used for the components described above could be any biocompatible material or construction, according to principles known in the art. Some examples include, but are not limited to medical grade stainless steel, titanium, titanium alloys, aluminum, aluminum alloys, chrome cobalt, pyrolytic carbon, polymers or ceramics. The materials should have adequate properties, such as shear and/or tensile strength, to perform their required functions. In addition, the materials may be coated and/or encapsulated with a biocompatible material.

The discussion above generally describes components and a procedure in which components are assembled together in the order of: brush; then slider; then handle. With appropriate modification to the components, a less preferred sequence could be: brush; then handle; then slider. That is, a possible configuration is for the slider to be advanced entirely through the handle after the handle is initially attached to the brush, followed by final locking of the handle in place on the combination of tamp and slider. Rotation and/or translation of the assembly would follow as described above.

In the context of the discussion above, to "advance" a component means to move it at least partially, and thus the term should not be read as implying that the component must reach (or has reached) its final intended location, unless specifically stated or clearly required by context.

In accordance with common and accepted clinical usage of orthopedic tools, the components described above may be repeatedly sterilized and reused. It is possible, but not preferred to produce components indicated only for single use (because of contact with body fluids).

While the Figures illustrate various embodiments of the apparatus, and describe it in the context of various embodiments of the method, the above description and the figures should be understood as exemplary in nature and not limited to the apparatus illustrated or the method specifically described by (or implied by) such embodiments.

We claim:

1. An apparatus for insertion into a void within cancellous bone interior to a vertebrae, comprising:
   a tamp including a distal end configured to be advanced into the void and an elongate shaft, at least a portion of the distal end of the tamp being configured to address a first portion of the cancellous bone surrounding the void when the tamp extends along a first longitudinal axis at a first position; and
   a slider configured to be distally advanced over at least a portion of the tamp such that the tamp moves from the first position to a second position along a second longitudinal axis parallel to the first longitudinal axis, the distal end of the tamp being radially extended when the slider is distally advanced over the portion of the tamp such that the portion of the distal end of the tamp addresses a second portion of the cancellous bone surrounding the void, the void being enlarged when the second portion of the cancellous bone surrounding the void is addressed by the portion of the distal end of the tamp.

2. The apparatus of claim 1, further comprising:
   a handle separately attachable to the combination of the tamp and the slider when the slider has been distally advanced over the portion of the tamp.

3. The apparatus of claim 1, further comprising:
a handle attached to a proximal end of the tamp prior to the slider being distally advanced through an opening of the handle and then over the portion of the tamp.

4. The apparatus of claim 3, wherein a rotatable cap is coupled to a proximal end of the slider, the cap configured to engage the handle when the cap is rotated to cause the distal end of the tamp to extend radially.

5. The apparatus of claim 1, further comprising:
a working cannula defining a lumen configured to receive at least a distal end portion of the combination of the tamp and the slider.

6. The apparatus of claim 1, wherein the tamp defines a first notch configured to be aligned with a notch of the slider when the slider has been distally advanced over the portion of the tamp.

7. The apparatus of claim 1, wherein the distal end of the tamp includes an end stop configured to limit distal advancement of the distal end of the slider with respect to the distal end of the tamp.

8. The apparatus of claim 1, wherein the portion of the distal end of the tamp includes a textured surface.

9. The apparatus of claim 1, wherein the portion of the distal end of the tamp has a first cross-sectional height, a portion of the tamp slidably disposed within the channel of the slider having a second cross-sectional height less than the first cross-sectional height.

10. An apparatus for advancement through a cannula, comprising:
a tamp comprising a distal textured surface and an elongate shaft, the tamp having a cross-sectional profile, the tamp having a length disposed at a first position along a first longitudinal axis when the tamp is introduced into the cannula;
a slider defining a channel configured to be slidably disposed on at least a portion of the tamp, at least a portion of the channel having a cross-sectional profile complementary to the cross-sectional profile of the tamp such that the slider is matingly engaged with the tamp when the channel of the slider is slidably disposed on the portion of the tamp, the length of the tamp being disposed at a second position along a second longitudinal axis different from and parallel to the first longitudinal axis when the channel of the slider is slidably disposed on the portion of the tamp;
the slider and the tamp are configured, when the channel of the slider is slidably disposed on the portion of the tamp, to be at least partially and rotatably disposed within a lumen of a cannula, such that (1) a distal end of the tamp is extended from a distal end of the lumen of the cannula into a void within cancellous bone of a vertebrae, and (2) linear alignment of the slider and the tamp within the lumen of the cannula causes the distal end of the tamp to extend radially to address the cancellous bone.

11. The apparatus of claim 10, further comprising:
a handle configured to enable at least one of rotational motion and translational motion of the tamp and the slider, in combination, within the cannula.

12. The apparatus of claim 11, wherein the handle is adapted to attach to the combination of the tamp and the slider.

13. The apparatus of claim 12, wherein a rotatable cap is disposed on a proximal end of the slider, the cap configured to engage the handle to cause the tamp to extend radially.

14. The apparatus of claim 11, wherein the handle is mounted on a proximal end of the tamp prior to advancement of the slider.

15. The apparatus of claim 10, wherein the distal end of the tamp includes an end stop configured to limit distal movement of the slider with respect to the distal end of the tamp.

16. The apparatus of claim 10, wherein the slider has a first length, the tamp has a second length greater than the first length.

17. The apparatus of claim 10, wherein:
a radial dimension of the tamp and slider in combination exceeds an inner diameter of the cannula.

* * * * *